US012751723B2

(12) United States Patent
Naybour et al.

(10) Patent No.: US 12,751,723 B2
(45) Date of Patent: Oct. 6, 2026

(54) ASSEMBLY FOR USE IN KNEE SURGERY

(71) Applicant: Eventum Orthopaedics Limited, Redvers Close (GB)

(72) Inventors: John Naybour, Redvers Close (GB); Paul Atherton, Redvers Close (GB); Jonathan Gonzalez, Redvers Close (GB)

(73) Assignee: Eventum Orthopaedics Limited, Redvers Close (GB)

(*) Notice: Subject to any disclaimer, the term of this patent is extended or adjusted under 35 U.S.C. 154(b) by 162 days.

(21) Appl. No.: 18/667,860

(22) Filed: May 17, 2024

(65) Prior Publication Data

US 2024/0307073 A1 Sep. 19, 2024

Related U.S. Application Data

(63) Continuation of application No. PCT/GB2022/052907, filed on Nov. 16, 2022.

(30) Foreign Application Priority Data

Nov. 22, 2021 (GB) ..................................... 2116779

(51) Int. Cl.
*A61B 17/15* (2006.01)
*A61B 17/08* (2006.01)
(Continued)

(52) U.S. Cl.
CPC ............ *A61B 17/158* (2013.01); *A61B 17/08* (2013.01); *A61B 17/1707* (2013.01); *A61B 17/14* (2013.01);
(Continued)

(58) Field of Classification Search
CPC .............. A61B 17/158; A61B 17/1677; A61B 17/1767; A61F 2/3877
See application file for complete search history.

(56) References Cited

U.S. PATENT DOCUMENTS 5,021,055 A * 6/1991 Burkinshaw ......... A61B 17/158 606/88
6,190,391 B1 * 2/2001 Stubbs ................... A61B 17/88 606/92
(Continued)

FOREIGN PATENT DOCUMENTS

EP 2540233 A1 1/2013
WO 2019006370 A1 1/2019
WO WO-2021240135 A1 * 12/2021 ........... A61B 5/4585

OTHER PUBLICATIONS

International Search Report and Written Opinion dated Jan. 30, 2023 for PCT Application No. PCT/GB2022/052907.
(Continued)

*Primary Examiner* — Matthew J Lawson
(74) *Attorney, Agent, or Firm* — EIP US LLP

(57) ABSTRACT

An assembly for use in knee surgery includes a patella sensor component having a backing plate and a sensor which generates a signal corresponding to compressive load applied to the backing plate, and shims providing a patella bearing surface for articulation against a surface on the femur, and positionable to define positions of the bearing surface relative to the patella. The assembly includes a clamp providing a reference surface for engaging the posterior surface of the patella and a support surface for supporting the head of a cutting instrument. Locator inserts are mounted on the clamp to define positions of the support surface relative to the reference surface, and define positions for the resection plane relative to posterior surface of the patella. The increment between the positions of the bearing surface relative to the patella matches the increment between the positions of the support surface relative to the reference surface.

9 Claims, 11 Drawing Sheets

(51) Int. Cl.

| | |
|---|---|
| ***A61B 17/16*** | (2006.01) |
| ***A61B 17/17*** | (2006.01) |
| *A61B 17/14* | (2006.01) |
| *A61F 2/46* | (2006.01) |

(52) U.S. Cl.
CPC ... *A61B 17/1677* (2013.01); *A61F 2002/4666* (2013.01)

(56) References Cited

U.S. PATENT DOCUMENTS

| | | | | |
|---|---|---|---|---|
| 7,097,662 | B2 * | 8/2006 | Evans, III ............ | A61B 5/1076<br>623/18.11 |
| 9,131,974 | B1 * | 9/2015 | Boyer ................ | A61B 17/1767 |
| 11,642,138 | B2 * | 5/2023 | Petteys ................ | A61B 17/158<br>606/88 |
| 2006/0142777 | A1 * | 6/2006 | Bastian ................ | A61B 17/158<br>606/88 |
| 2012/0310246 | A1 * | 12/2012 | Belcher ................ | A61F 2/4684<br>606/89 |
| 2013/0030443 | A1 * | 1/2013 | Wright ................ | A61B 17/158<br>606/96 |
| 2021/0137704 | A1 * | 5/2021 | Angibaud ............. | A61F 2/4684 |
| 2023/0404598 | A1 * | 12/2023 | Steeven ............. | A61B 17/1767 |
| 2025/0114104 | A1 * | 4/2025 | Snauwaert ............ | A61F 2/3877 |

OTHER PUBLICATIONS

Combined Search and Examination Report dated Jun. 17, 2022 for GB Application No. GB2116779.6.

* cited by examiner

ASSEMBLY FOR USE IN KNEE SURGERY

CROSS-REFERENCE TO RELATED APPLICATIONS

This application is a continuation under 35 U.S.C. § 120 of International Application No. PCT/GB2022/052907, filed Nov. 16, 2022, which claims priority to United Kingdom Application No. GB 2116779.6, filed Nov. 22, 2021, under 35 U.S.C. § 119(a). Each of the above-referenced patent applications is incorporated by reference in its entirety.

BACKGROUND

This invention relates to an assembly for use in knee surgery.

Some knee replacement procedures include replacement of the portion of the patella which acts against the femur during articulation of the joint with a patella implant component. Replacement involves removing the surface part of the patella which acts against the femur to prepare the patella to receive the patella implant component. The patella implant component has a bearing surface which is shaped to act against the femur, with a generally domed portion which facilitates sliding of the patella along the trochlear groove.

Successful implantation of a knee prosthesis relies on accurate positioning of the components of the prosthesis. Anterior knee pain and functional deficit in the implanted prosthesis can result from muscle imbalances or from poor alignment and incorrect positioning of the prosthesis components, especially the femoral and patella components. Factors which can give rise to these problems include patellofemoral instability, mis-positioning of the femoral component along the anterior-posterior axis, and internal-external rotation of the femoral component.

WO-A-2019/006370 discloses a patella kit which includes a conformable sensing device for fitting on to the articulating surface of a patella. The sensing device is fitted to the patella before any resection step. The kit includes a set of trial implants which can be fitted to the patella after it has been resected, and a set of implants which match corresponding ones of the trial implants. A computer is used to compare joint reaction force data from the sensing device so that a patella implant component can be selected which optimises the function of the joint after implantation.

The disclosed kit is discussed only in relation to a surgical procedure in which the patella is resected once and trial implants are fitted to that resected patella surface in turn. The trial implants and the implants can differ from one another in terms of their diameters, thicknesses and angulations. In one embodiment, an implant kit includes implants with four anatomical sizes, three thickness options and two angulation options, resulting in twenty-four patella implants and corresponding trials.

This invention provides an assembly for use in knee surgery which comprises:

a. a patella sensor component comprising:
   i. a backing plate which can be fitted to the patella and which has at least one sensor which can generate a signal corresponding to the compressive load applied to the backing plate,
   ii. at least first and second shims which provide a patella bearing surface for articulation against a surface on the patient's femur, and which can be positioned individually or in one or more combinations between the backing plate and the patient's patella to define first and second positions of the bearing surface relative to the patella,
b. a cutting instrument having a cutting head for cutting the patella on a selected resection plane,
c. a clamp for a patella having opposing jaws which can be moved towards one another to clamp the patella between them, the clamp providing:
   i. a reference surface for engaging the posterior surface of the patella,
   ii. a support surface for supporting the cutting head of the cutting instrument, thereby locating the cutting instrument relative to the clamp,
d. at least first and second locator inserts which can be mounted individually or in one or more combinations on or relative to the clamp, providing a physical connection between the reference and support surfaces which define first and second positions of the support surface relative to the reference surface, and thereby define first and second positions for the resection plane relative to posterior surface of the patella, in which the increment between the first and second positions of the bearing surface on the bearing plate relative to the patella matches the increment between the first and second positions of the support surface relative to the reference surface.

The invention makes use of a sensor in combination with a set of shims to vary the effective thickness of the sensor or the angle between its principal faces or both, in combination with a matching set of inserts which can be used on the clamp to set the distance between the reference and support surfaces or the angle between them or both. The distance between the reference and support surfaces and the angle between them can be set to match the effective thickness and angle between the principal surfaces of the patella sensor component by appropriate selection of inserts.

The invention can be used to optimise the location (effectively corresponding to the thickness of the portion of the patella that is removed in the resection step) and inclination of the plane on which a patella is resected to receive a patella implant component so that anterior pain and functional deficit in the joint after surgery are minimised. The optimised location and inclination of the resection plane which receives the patella implant component are identified using force data from the sensor (or sensors). The assembly includes shims for use with the sensor and corresponding locator inserts which define relative positions for a reference surface which contacts a surface of the patella and a support surface for the cutting head of a cutting instrument such as a saw or a reamer. A surgeon is therefore able to identify a locator insert which will provide a desirable location and inclination of the resection plant for receiving a patella implant component with reference to the shim or shims used with the sensor to provide a force data profile which is recognised by the surgeon as optimum. The invention therefore allows the forces acting on the patella (which incorporates a patella implant component) during articulation of the knee after surgery to be optimised by optimising the position (location and inclination) of the plane on which the patella is resected to receive that implant component. The invention removes the need to provide the surgeon with multiple patella implant components and associated trial components. This simplifies the kit which is supplied for a procedure and reduces costs. The invention can also be seen as enabling a simplified procedure.

Optionally, the assembly can include a third shim which can be used to define a third position of the bearing surface on the bearing plate relative to the patella, and a third locator insert which can be used to define a third position of the bearing surface on the bearing plate relative to the patella, in which the increment between the second and third positions of the bearing surface on the bearing plate relative to the patella matches the increment between the second and third positions of the support surface relative to the reference surface, and therefore of the resection plane relative to the patella. The assembly can include further shims and locator inserts.

Optionally, the thickness of the second shim is greater than the thickness of the first shim, and the difference in thickness between the first and second shims matches the difference between the distances between the reference surface and the support surface when in their first and second relative positions.

Optionally, the difference in thickness between the first and second shims might be at least about 0.5 mm, or at least about 0.75 mm. The difference between the distances between the reference surface and the support surface when in their first and second relative positions might then be at least about 0.5 mm, or at least about 0.75 mm, respectively. The difference in thickness between the first and second shims might be not more than about 2 mm, or not more than about 1.5 mm, or not more than about 1.25 mm. The difference between the distances between the reference surface and the support surface when in their first and second relative positions might then be not more than about 2 mm, or not more than about 1.5 mm, or not more than about 1.25 mm, respectively. For example, the difference in thickness between the first and second shims might be about 1 mm. The difference between the distances between the reference surface and the support surface when in their first and second relative positions might then be about 1 mm.

Optionally, each shim has principal opposite surfaces and the angle between the principal surfaces of the second shim is greater than the angle between the principal surfaces of the first shim, and the difference between the angles between the principal surfaces of the first and second shims matches the difference between the angles between the reference surface and the support surface when in their first and second relative positions. When a principal surface of a shim is non-planar, the plane defined by that surface can be identified with reference to its edge.

Optionally, the difference between the angles between the principal surfaces of the first and second shims might be at least about 1° or at least about 2°. The difference between the angles between the reference surface and the support surface might then be at least about 1° or at least about 2°, respectively. The difference between the angles between the principal surfaces of the first and second shims might be not more than about 4° or not more than about 3°. The difference between the angles between the reference surface and the support surface might then be not more than about 4° or not more than about 3°, respectively. For example, the difference between the angles between the principal surfaces of the first and second shims might be about 2.5°. The difference between the angles between the reference surface and the support surface might then be about 2.5°.

It can be preferred for the shims to include markings or other indicia (for example colour coding) to aid identification. The markings on a shim might provide an indication of its thickness (for example an indication of its relative thickness compared with a different shim), or the angle between its opposite principal surfaces, or both.

It can be preferred for the locator inserts to include markings or other indicia (for example colour coding) to aid identification. The markings on a locator insert might provide an indication of the distance between the reference surface and the support surface that results from use of that insert (for example an indication of the relative distance compared with the distance that results from use of a different insert), or the angle between the reference and support surfaces that results from use of that insert, or both.

Optionally, each of the first and second locator inserts comprises a connector insert which can be mounted on the clamp and a spacer insert which can be mounted on the connector insert. Optionally, the angular orientation of the support surface relative to the reference surface can be varied by changing one or more of the connector inserts. Optionally, the distance between the support surface and the reference surface can be varied by changing one or more of the spacer inserts.

Optionally, each of the first and second shims has principal opposite surfaces and the angle between the principal surfaces of the second shim is greater than the angle between the principal surfaces of the first shim. The difference between the angles between the reference surface and the support surface when the first and second connector inserts respectively are mounted on the clamp can then match the difference between the angles between the principal surfaces of the first and second shims. Similarly, when the assembly includes a third shim and a third connector insert, the difference between the angles between the reference surface and the support surface when the second and third connector inserts respectively are mounted on the clamp can then match the difference between the angles between the principal surfaces of the second and third shims.

Optionally, the thickness of the second shim is greater than the thickness of the first shim and the assembly includes first and second spacer inserts. The difference between the distances between the reference surface and the support surface when the first and second spacer inserts respectively are mounted on the clamp can then match the difference between the thicknesses of the first and second shims. Similarly, when the assembly includes a third shim and a third spacer insert, the difference between the distances between the reference surface and the support surface when the second and third spacer inserts respectively are mounted on the clamp can then match the difference between the thicknesses of the second and third shims.

Optionally, the assembly includes a plurality of spacer inserts which can be mounted individually or in one or more combinations on or relative to the clamp, providing a physical connection between the reference and support surfaces so that the distance between the support surface and the reference surface can be varied by changing one or more of the spacer inserts. The variation in the distance between the support and reference surfaces in the clamp allows the amount of bone that is removed using the cutting instrument to be varied by changing one or more spacer inserts. This variation in the depth of the cut (so that, for example, a deeper cut results in the removal of more bone from the patella) is an option together with the variation in the inclination of the cut as discussed above.

Optionally, a connector insert can be double ended so that the difference between the angle between the support surface and the reference surface that is defined by a first end of the connector insert and zero is half of the difference between the angle between the support and reference surfaces that is defined by the first end of the connector insert and the angle between the support and references surfaces that is defined by the second end of the connector insert. For example one end of a connector insert might define an angle between the support and reference surfaces which is +2.5° and the other end of a connector insert might define an angle which is −2.5°, or one end of a connector insert might define an angle between the support and reference surfaces which is +1.25° and the other end of a connector insert might define an angle which is −1.25°.

The support surface can be fixed relative to the clamp. For example, the support surface might be provided by a surface of the clamp. An example of a support surface that is provided by a surface of the clamp could be a planar surface which is provided by an arm which extends adjacent to the patella when it is held within the clamp in the normal position. The arm might be a part of a frame which extends at least part way around the patella when held within the clamp. The support surface can be an open surface so that a cutting head is not restrained from moving away from the support surface. The support surface can be a closed surface so that movement of the cutting head to separate it from the support surface is restricted. This can be achieved when the support surface is provided by an internal surface of a slot.

A cutting assembly can be used in a method of knee replacement surgery which comprises:

a performing a first resection on the patient's patella, b. fitting to the resected patella a patella sensor component comprising:

i. a backing plate having at least one sensor which can generate a signal corresponding to the compressive load applied to the backing plate, and ii. a first shim which can be fitted to the backing plate and which, when fitted to the backing plate, provides a bearing surface for articulation with a bearing surface on the patient's femur, c. articulating the knee joint to obtain information from the sensor concerning tension in soft tissue which is connected to the patella as the patella articulates against the patient's existing femoral bearing surface, d. fitting a femoral component to the patient's femur, e. articulating the knee joint to obtain information from the sensor concerning tension in soft tissue which is connected to the patella as the patella articulates against the surface provided by the femoral component, f. identifying the location and inclination of a second resection of the patella to receive a patella implant component whose thickness is greater than that of the patella sensor component, to provide a desired tension in soft tissue which is connected to the patella as the patella articulates against the femoral implant component in the completed replacement joint, g. performing the second resection on the patient's patella, and h. fitting the patella implant component to the patient's patella.

This method makes possible the selection of an appropriate soft tissue tension after surgery because the thickness of the patella sensor component is not more than that of the patella implant component (and of a patella trial component having a configuration which matches that of the implant component). This means that the amount of tissue that is removed from the patella in a first resection to allow the patella sensor component to be fitted against the patella is not more, and generally is less, than the total amount of tissue that might be removed from the patella after a second resection which then allows the patella implant component to be fitted. The patella fitting will accommodate changes in the position or inclination or both of the femoral bearing surface in the implanted knee prosthesis compared with the femoral bearing surface in the joint prior to surgery. Such changes can be detected using the patella sensor component which can be used to monitor the compressive forces which are imposed on the sensor component between the patella and the femoral bearing surface, resulting from soft tissue by which the patella is held in place and pressed against the femoral bearing surface. The method provides the possibility of comparing the compressive forces at the patellofemoral interface between (a) the femoral bearing surface prior to surgery (which will be provided by the native femur in a primary knee replacement procedure, or a surface of a previously implanted femoral component in a revision procedure, or a surface provided by a femoral component (trial or implant) positioned during surgery), and (b) the femoral bearing surface provided during the surgery by a trial femoral component or a femoral implant component. It can be desirable in order to optimise the surgical outcome to minimise the differences between the measured compressive forces. This can be done by appropriate selection of the depth of the resection of the patella: a deeper resection to remove relatively more patella tissue results in reduced compressive forces. Differences in the compressive forces in one or more regions of the patella can be reduced by varying the inclination of the patella resection, for example by increasing its depth medially more than laterally, or laterally more than medially, or superiorly more than inferiorly, or inferiorly more than superiorly, or combinations thereof. The invention enables forces in soft tissue connected to the patella to be adjusted by changing the effective depth of the patella so as to accommodate changes in the anterior-posterior position of the femoral bearing surface.

The support surface might be provided by a support component which can move relative to the clamp. For example a support component might be capable of being fixed to a clamp in a desired position and orientation. This can be advantageous when access to a patella to fasten a clamp to it is restricted, resulting in the clamp possibly being aligned incorrectly. Proper alignment of the support surface can then be achieved by movement of the support component so that the support surface is in a desired position and orientation.

Optionally, the backing plate and the shims include cooperating engagement features by which shims can be fastened to the backing plate. The engagement features can comprise resiliently deformable fingers on the backing plate or the shims, each having at least latch at its end. Such fingers might deform in a bending mode when the backing plate and a shim are pressed together, and then spring back towards the undeformed configuration once the backing plate and the shim are fully engaged, for example with the latch received in a detent or a groove or against some other surface. The detent or groove can extend continuously around the entire periphery of the component. A plurality of detents can be provided for engagement by respective latched fingers. The number of detents can be equal to the number of latched fingers. Preferably the detents are spaced apart equally and the spacing matches that of the latched fingers. This allows the backing plate to have a shim mounted on it in multiple rotational orientations. The number of detents can be a multiple of the number of latched fingers so that the detents define multiple relative rotational orientations of the backing plate and the shims. For example, when there are four latched fingers, there might be four spaced apart detents allowing four rotational orientations, or eight detents allowing eight rotational orientations.

Optionally, the assembly includes a patella implant component and optionally also a trial patella component.

The assembly can be used with cutting assembly for resecting a patient's patella during knee surgery, which comprises:

a. a cutting instrument having a cutting head for cutting the patella on a selected resection plane,
b. a clamp for a patella having opposing jaws which can be moved towards one another to clamp the patella between them, the clamp providing:
   i. a reference surface for engaging the posterior surface of the patella,
   ii. a support surface for the cutting instrument relative to the clamp, in which the assembly includes a connector arrangement which provides a physical connection between the reference and support surfaces to define the inclination of the support surface relative to the reference surface, and which can be adjusted to vary the inclination of the support surface relative to the reference surface.

The connector arrangement can comprise a plurality of connector inserts which can be mounted individually or in one or more combinations on or relative to the clamp, providing a physical connection between the reference and support surfaces which defines the inclination of the support surface relative to the reference surface, and in which variation of the inclination of the support surface relative to the reference surface involves changing one or more of the connector inserts that are mounted on or relative to the clamp.

Such an assembly can enable the inclination of a cutting instrument relative to a patella which is held during a cutting step by means of a clamp to be varied so that the inclination (and optionally also the location (or depth)) of the patella surface which is created using the cutting instrument can be varied. This can be achieved by adjusting the connector arrangements (for example by changing one or more connector inserts mounted on or relative to the clamp) to vary the spatial relationship of the reference surface relative to the support surface. The variation can involve the angle of the cut so that the cut might be deeper towards the medial edge of the patella than towards the lateral edge, or deeper towards the lateral edge of the patella than towards the medial edge, or deeper towards the superior edge of the patella than towards the inferior edge, or deeper towards the inferior side of the patella than towards the superior edge. The variation can involve a combination of medial/lateral and superior/inferior inclinations.

Optionally, the cutting head is a saw blade. Optionally, the clamp has a slot formed in it which the saw blade can move in with a reciprocating action, and the support surface is provided within the slot.

The cutting instrument can be a reamer with a rotating cutting head which can be directed towards the patella to remove tissue and so create a resected surface. The support surface can be provided by a collar which defines a bore. The cutting head can be inserted through the bore to engage the patella until a flange surface on the reamer engages an axially facing edge of the collar to prevent further movement of the cutting head towards the patella. The axially facing edge of the collar can then function as the support surface. The use of such depth stop arrangements in conjunction with surgical reamers is known.

The clamp for the patella will frequently have opposing jaws which can be moved towards one another to clamp the patella between them. The clamp jaws can engage the patella on its anterior and posterior faces. However, it will often be preferred that the clamp jaws engage the patella on opposed edge surfaces. For example, the clamp might engage the patella on its medial and lateral edge surfaces. An example of a suitable instrument is the Premium Patella Saw Guide which is available from Enztech Limited of Christchurch, New Zealand. This instrument includes a stylus which extends over the posterior surface of the patella when the patella is engaged within the instrument and can be used as a point of reference when positioning the patella within the instrument. Inserts as provided in the assembly of the invention can be mounted on the stylus.

Optionally, each of the support surface and the reference surface is approximately planar. This will be appropriate when the surface of the patella which is exposed in the resection step is planar for fitting against it of a patella implant component having a planar patella engaging surface. This will frequently be the case.

The reference surface can have one or more openings formed in it, for example, to facilitate assembly of each spacer insert with one of the connector inserts or with the clamp.

Optionally, the clamp includes a mount and each of the connector inserts has a mount feature for engaging the mount to locate a selected connector insert on the clamp.

Optionally, the clamp includes a mount and each of the spacer inserts has a mount feature for engaging the mount to locate a selected spacer insert on the clamp.

For example, the mount can comprise a rod and each of a plurality of inserts (especially each of a plurality of connector inserts) can have a channel (for example, a bore) formed in it so that a selected insert can be located on the clamp by sliding the insert along the rod with the rod received within the channel.

Optionally, the mount can include a latch feature which can be engaged by an insert (such as a connector insert) which has been slid fully along the rod so that further movement of the insert along the rod is inhibited. For example, the latch feature can be a protrusion on the rod or other mount which is engaged by the insert with a snap fit. This might be achieved for example by means of a pair of jaws on the insert which can be opened to fit over the protrusion. At least the jaws on the insert can be made at least in part from a resiliently deformable material to facilitate opening of the jaws to fit over the protrusion.

Optionally, the assembly includes a first connector insert and a second connector insert, in which, when the first connector insert is mounted on or in relation to the clamp, the plane defined by the reference surface is approximately parallel to the plane defined by the support surface, and in which, when the second connector insert is mounted on or in relation to the clamp, the angle between the planes defined by the support and reference surfaces is greater than 0°. For example, the angle might be at least about 1°, or at least about 1.25°. Optionally, the angle is not more than about 4°, preferably not more than about 3°. For example the angle can be about 1.25° or about 2.5°.

Optionally, the assembly includes a neutral connector insert which can be mounted on or in relation to the clamp so that, when the neutral connector insert is mounted on or in relation to the clamp, the plane defined by the reference surface is approximately parallel to the plane defined by the support surface.

Optionally, the assembly includes:

a. a primary insert which can be mounted on or in relation to the clamp so that, when the primary insert is mounted on or in relation to the clamp, the plane defined by the reference surface is parallel to the plane defined by the support surface, and b. a plurality of spacer inserts which can be mounted individually or in one or more combinations on or relative to the clamp (with a connector insert in many embodiments), providing a physical connection between the reference and support surfaces which defines the distance between the support surface and the reference surface so that the distance between the support surface and the reference surface can be varied by changing one or more of the spacer inserts, in which the distance between the reference and support surfaces when the primary insert is mounted on the clamp is greater than the greatest of the distances between the reference and support surfaces that are available when any of the spacer inserts (together with a connector insert if provided) are mounted on the clamp.

A primary insert can be used in an initial stage of preparing a patella in which the patella is resected by removing a posterior portion of the patella including the patella bearing surface. When the primary insert is mounted on or in relation to the clamp, the plane defined by the reference surface will frequently be approximately parallel to the plane defined by the support surface, The resulting posterior planar surface of the patella can be used in a sensing step using the patella sensor component in which compressive forces on the sensor component between the patella and the femoral bearing surface, resulting from soft tissue by which the patella is held in place and pressed against the femoral bearing surface, can be monitored, and used to determine the depth and inclination of a second resection step. The location (or depth) of the second resection plane is determined by use with the clamp of a selected connector insert and a selected spacer insert. Sensors in a sensor component can be used to measure the effect of the tension in soft tissue and the position and magnitude of the intersegmental loads on the patella surface through the passive flexion cycle.

Optionally, each of the spacer inserts has a marking on it which is indicative of the distance between the support surface and the reference surface when that spacer insert is in use.

Optionally, the difference between the distance between the support surface and the reference surface that is defined by the first spacer insert and the distance between the support surface and the reference surface that is defined by the second spacer insert is at least about 0.5 mm, preferably at least about 0.8 mm. Optionally, the difference is not more than about 2 mm, preferably not more than about 1.5 mm. For example the difference can be about 1 mm.

Optionally, at least one of the support surface and the reference surface is provided by one of the spacer inserts when mounted on or in relation to the clamp. For example, when the reference surface is provided by a spacer insert, a patella can be positioned within the clamp by pressing the patella against the spacer insert reference surface.

Optionally, the reference surface (which can be provided on each of the spacer inserts, but might be provided by another element of the clamp) has a profile which matches at least approximately the profile of the posterior surface of the patella so that the reference surface sits stably on the patella. When the patella has been resected in an initial resection step (for example so that a patella sensor component can be fitted against it as described above), the surface of the patella which is engaged by the reference surface will be approximately planar. It will then be preferred that the reference surface is approximately planar.

Optionally, each of the connector inserts and each of the spacer inserts has a mateable connector feature for connecting a selected connector insert and a selected spacer insert to one another. For example, each of the connector inserts can have a first connector feature and each of the spacer inserts can have a second connector feature, which are arranged so that a first connector feature engages with a second connector feature to connect a selected connector insert to a selected spacer insert. It will often be preferred that the connector features on at least some of the connector inserts are the same, and that the connector features on at least some of the spacer inserts are the same, so that any one of the connector inserts can be connected to any one of the spacer inserts.

Optionally, the clamp includes a mount and each of the connector inserts has a location feature which can engage the mount and for mounting a selected connector insert on the clamp, and each of the connector inserts and each of the spacer inserts has a mateable connector feature for connecting a selected spacer insert to a selected connector insert which is mounted on the clamp. The connector insert can be selected to provide a desired angular relationship (or inclination) between the reference and support surfaces, and the spacer insert can be selected to provide a desired spacing between the reference and support surfaces. The patella sensor component can be used to measure the variation in tension in soft tissue connected to the patella during flexion, especially with shims which can be mounted on the patella sensor component to vary the effective thickness of the sensor component and/or the angle between its principal surfaces.

Optionally, each of the support surface and the reference surface is approximately planar and the assembly includes a first spacer insert and a second spacer insert, and the angle between the planes defined by the support and reference surfaces when the first spacer insert is connected to a selected connector insert is the same as the angle between the planes defined by the support and reference surfaces when the second spacer insert is connected to the selected connector insert.

The possibility that is provided by the invention of varying the inclination of the resection plane on the patella, or of the depth of the resection, or both, allows information to be obtained concerning the tension in the soft tissue which is connected to a patient's patella as the patella articulates against the patient's existing femoral bearing surface (which could be the bearing surface provided by the patient's native femur, or the bearing surface provided by an existing implanted femoral prosthesis component) using patella sensor component (which has been fitted to the patella after an initial resection of the patella to remove a thickness of bone which corresponds approximately to the thickness of the patella sensor component). This can be compared with information that is obtained subsequently, after fitting a femoral trial component to the femur or a femoral implant component, when the patella articulates against the surface provided by the femoral trial or implant component. The tension in the soft tissue can then be increased by changing to a thicker bearing plate in the trial patella component. The tension in the soft tissue can be reduced by changing to a thinner bearing plate in the trial patella component. The balance in the tension in soft tissue on different sides of the joint (for example between medial and lateral sides) can be varied by changing the inclination of the patella sensor component.

A surgeon can calculate the correct amount to resect from the patella in order to obtain a desired tension in the quadriceps muscle, for example to match the tension in the muscle prior to the operation, by changing the thickness and optionally also the inclination of the trial patella component by a known amount. The sensors can provide load signals to a data processing device which can store the load data. Information concerning the sensed load can be displayed on a display device such as a monitor. The effect of changing the thickness and/or the inclination of the trial patella component throughout the range of motion of the joint can be observed. This information can help the surgeon to assess the relative suitabilities of different surgical options. For example, it can help the surgeon to match the load applied to the trial patella component by selecting a bearing plate having an appropriate thickness and/or inclination. The amount of additional bone that should be resected from the patella, in order to accommodate the patella implant component can be calculated once the bearing plate with an appropriate thickness and/or inclination has been identified.

As an example, the distance between the reference and support surfaces when the primary insert is mounted might be at least about 4 mm, especially at least about 5 mm. The distance might be not more than about 8 mm, especially not more than about 7 mm, for example about 6 mm. This enables the assembly to be used in a resection step which results in a piece of bone having a thickness of 6 mm being removed from the patella, allowing a sensor component having a thickness of 6 mm to be positioned in the joint without changing the tension of soft tissue connected to the patella.

The spacer inserts can be arranged to define distances between the reference and support surfaces which are up to about 5 mm, or up to about 4 mm, or up to about 3 mm. An assembly can ideally include spacer inserts which define at least two distances between 1 mm and 4 mm (including the limits of the range). By way of example, when the primary insert results in a piece of bone having a thickness of 6 mm being removed and the selected spacer insert results in a piece of bone having a thickness of 2 mm being removed, the total amount of bone removed will have a thickness of 8 mm. If the patella implant component that is then used has a thickness of 9 mm, the tension in soft tissue will be reduced, which can be advantageous when the result of implanting a femoral joint component is to move the femoral bearing surface anteriorly.

The spacer inserts or the connector inserts can be made from polymeric material. Examples of suitable polymeric materials include polyolefins such as polyethylene and polypropylene, polyamides and polyesters, optionally with fibre reinforcement. The use of polymeric materials has the advantage of low cost and ease of manufacture by injection or other moulding processes, or by additive layer manufacturing (3-d printing). In addition, inserts can be designed so that, when made from polymeric materials, they include flexible portions which can function is living hinges, especially so that they can flex resiliently, so that they can function as latches.

INTRODUCTION TO THE DRAWINGS

The invention is described below by way of example with reference to the accompanying drawings, in which.

Figure 1:
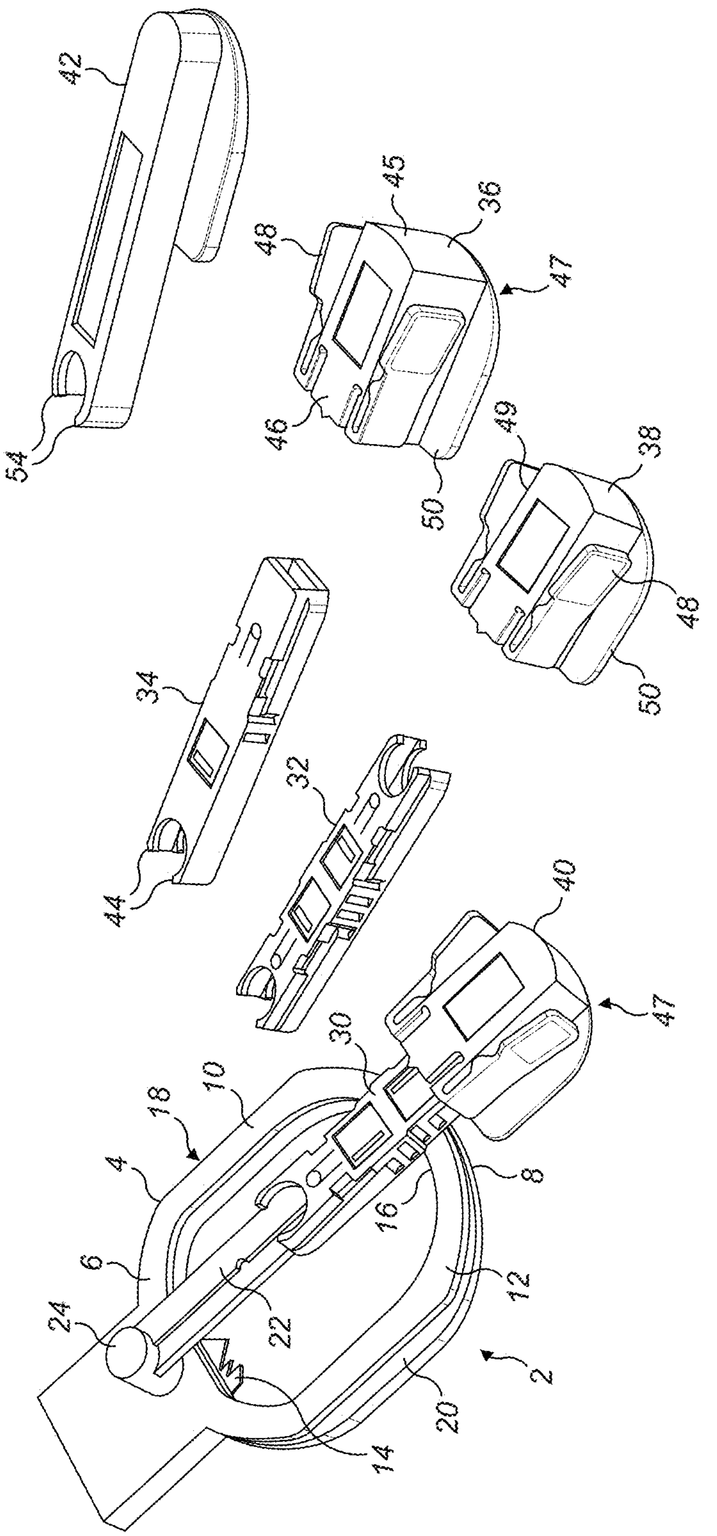
FIG. 1 is an isometric view of a clamp and primary, connector and spacer inserts of a cutting assembly which can be used to resect a patient's patella during knee surgery.

FIGS. 5*a*-5*g* are enlarged isometric views showing a primary insert, and the sets of connector and spacer inserts shown in FIG. 1.

Figure 5A:
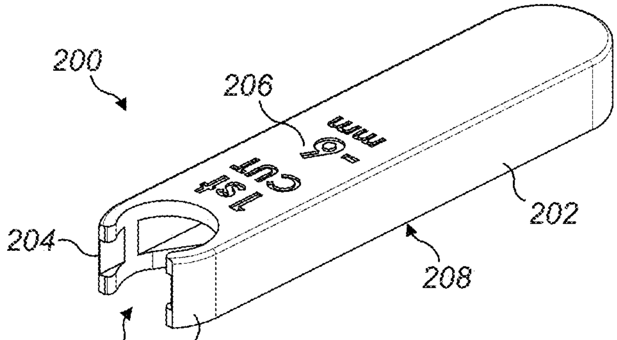
Figure 5B:
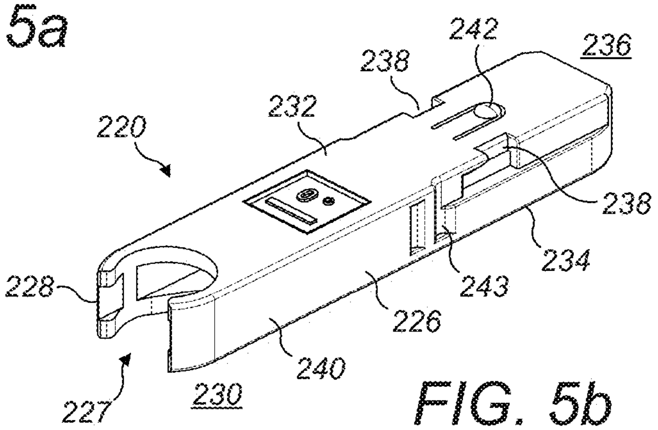
Figure 5C:
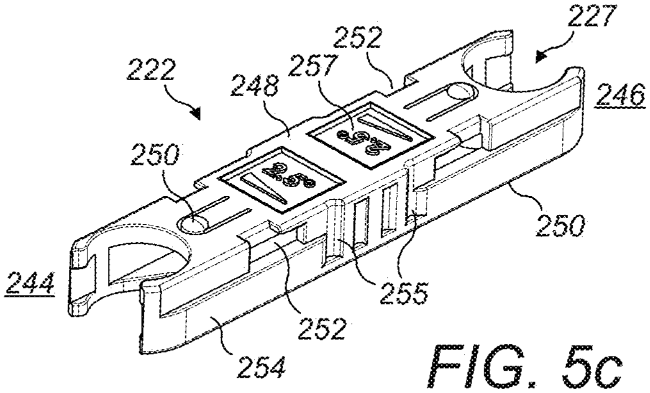
Figure 5D:
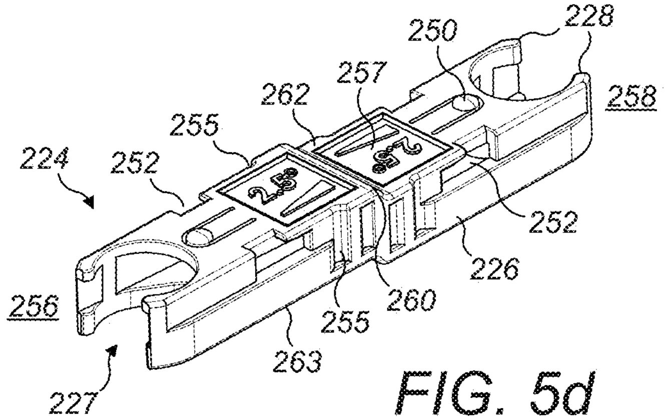
Figure 5E:
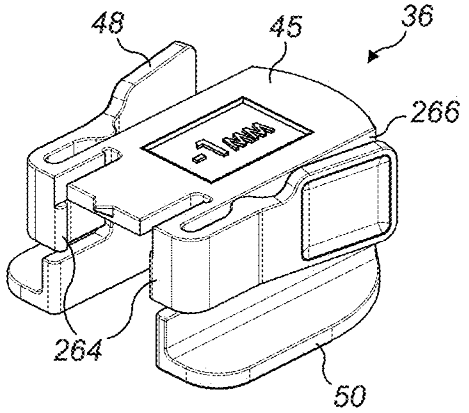
Figure 5F:
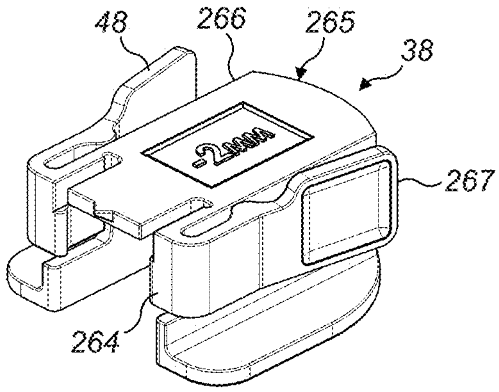
Figure 5G:
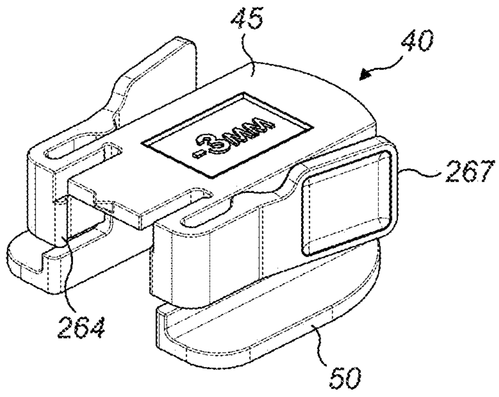
Figure 6A:
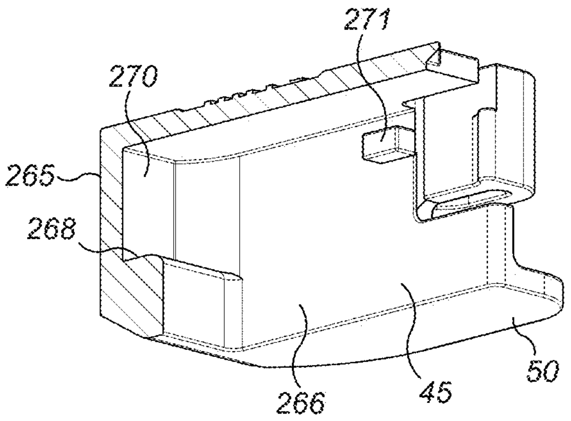
Figure 6B:
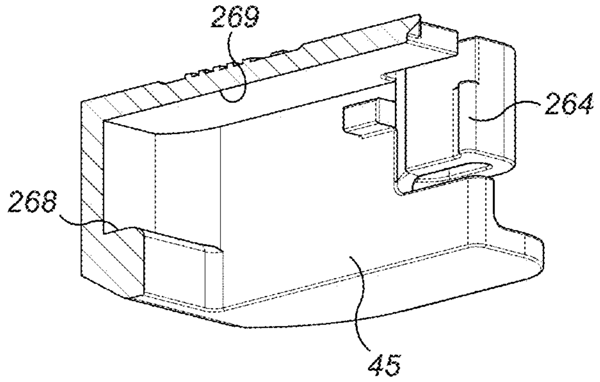
Figure 6C:
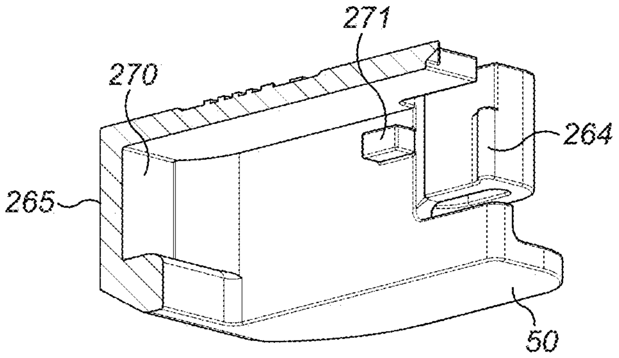

FIGS. 6*a*-6*c* are isometric sectioned views of the spacer inserts shown in FIGS. 1 and 5.

Figure 7:
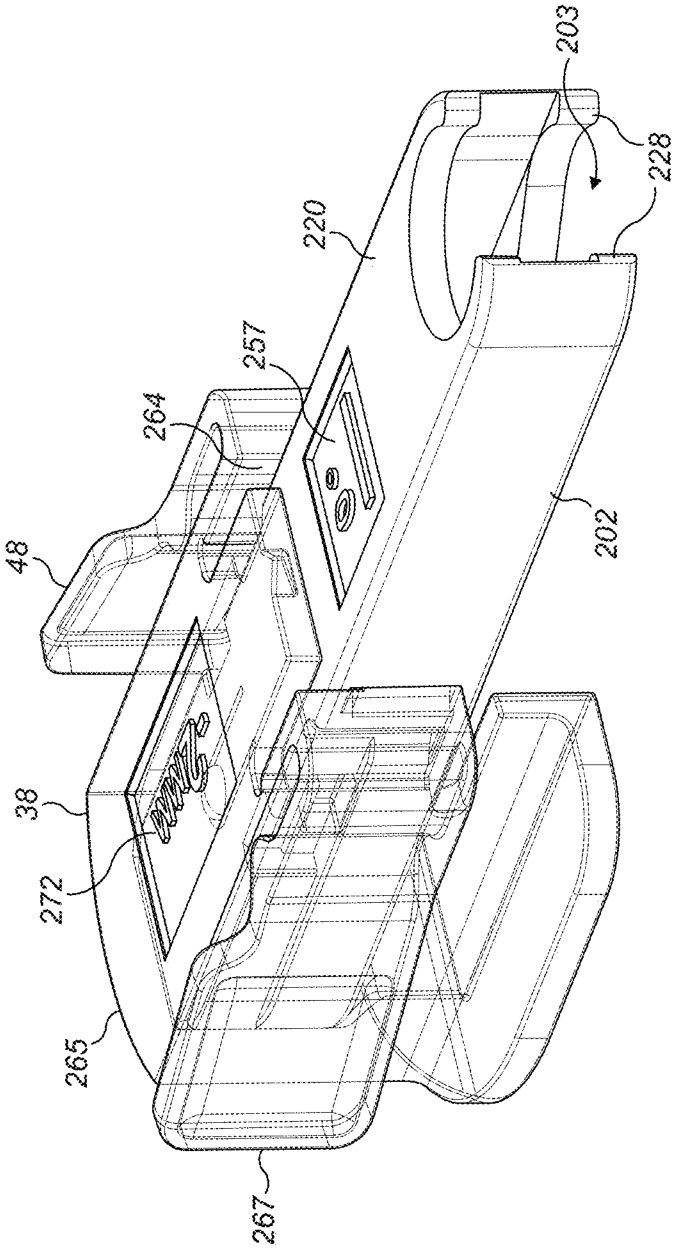

FIG. 7 is an isometric view showing a connector insert, with a spacer insert shown in phantom mounted on the connector insert.

Figure 8:
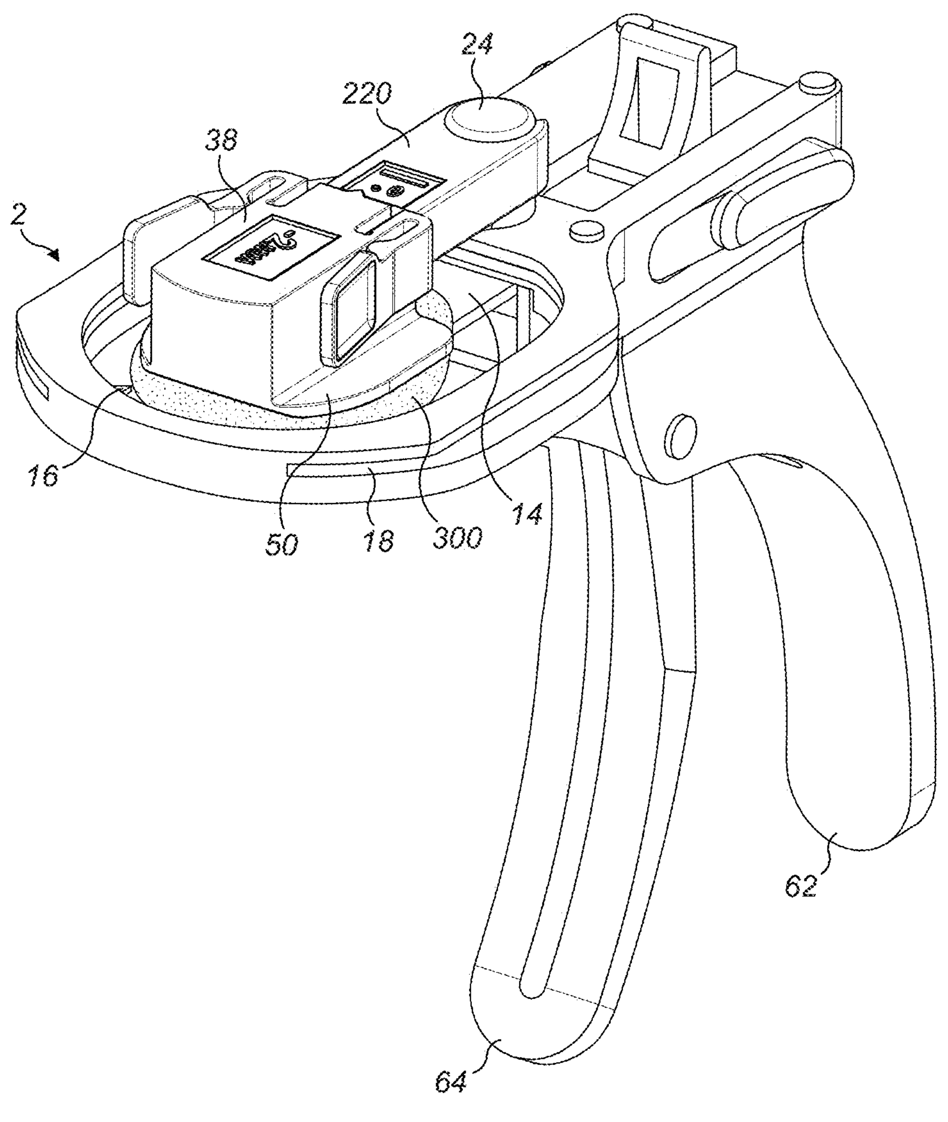

FIG. 8 is an isometric view showing the connector and spacer inserts shown in FIG. 7, mounted on the clamp.

Figure 9A:
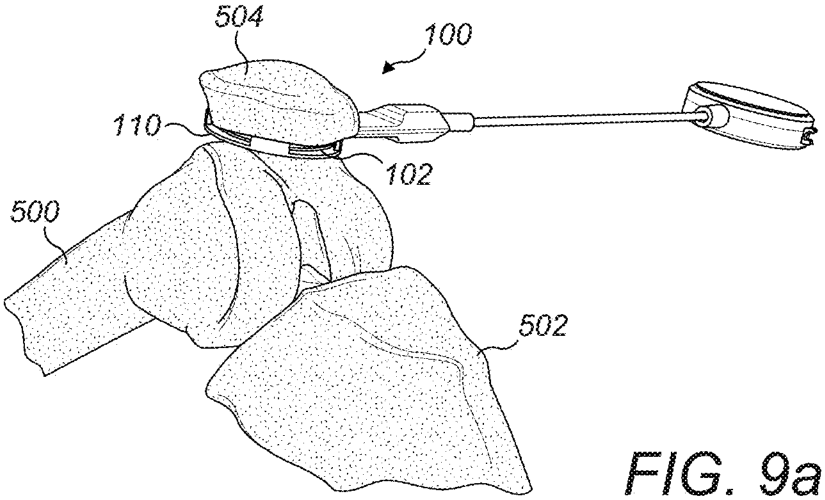
Figure 9B:
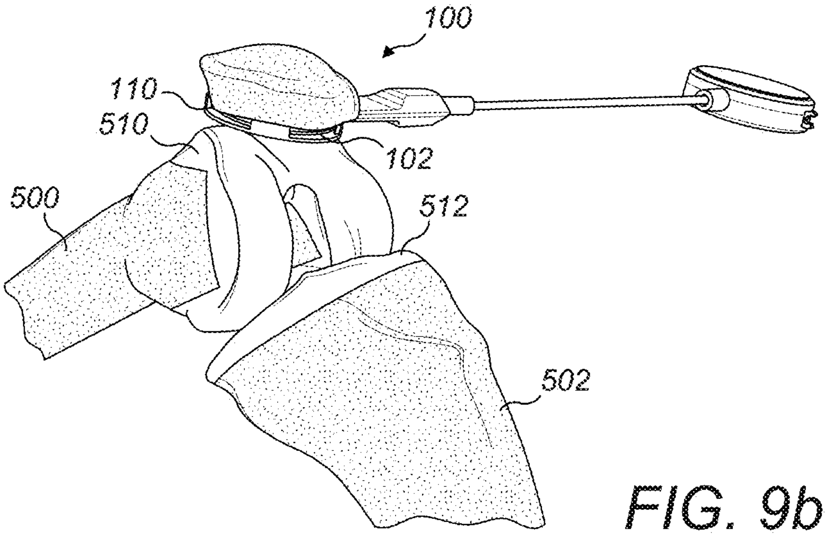
Figure 9C:
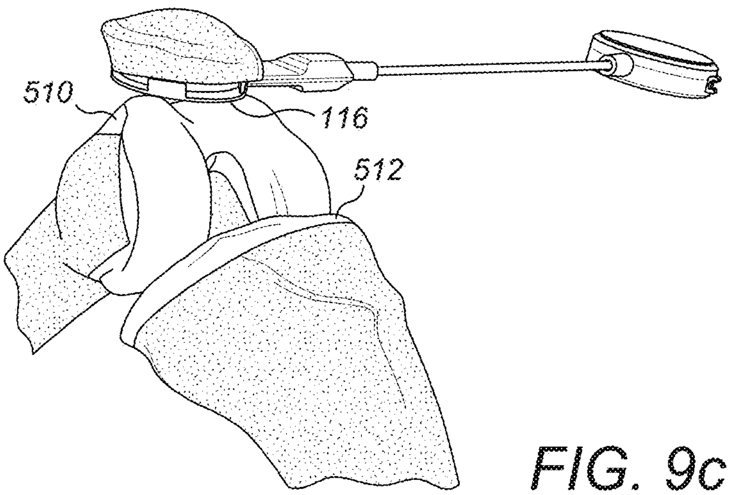

FIGS. 9*a* to 9*c* are medial views of a patient's knee, with a sensor component positioned between the patella and the femur, at three stages in a knee replacement procedure.

Figure 10A:
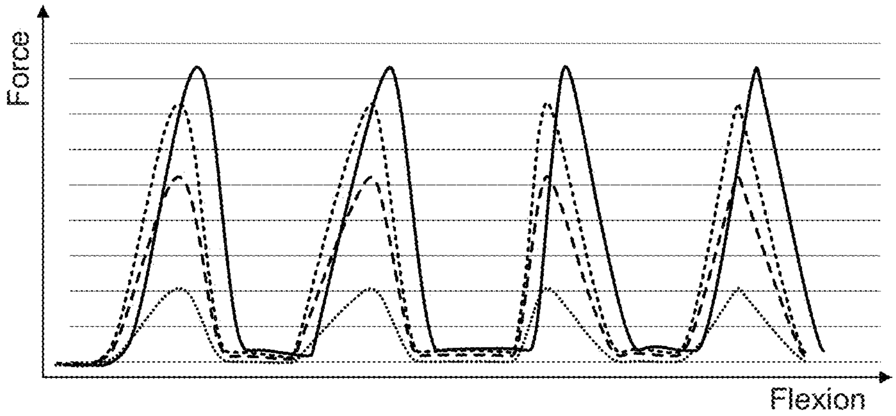
Figure 10B:
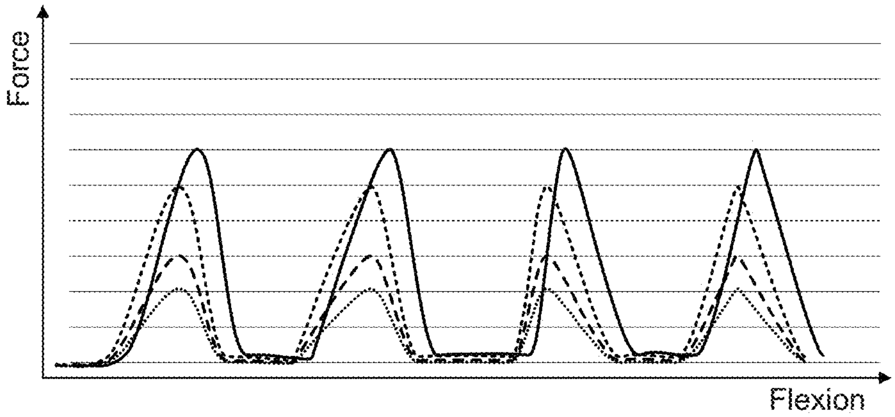
Figure 10C:
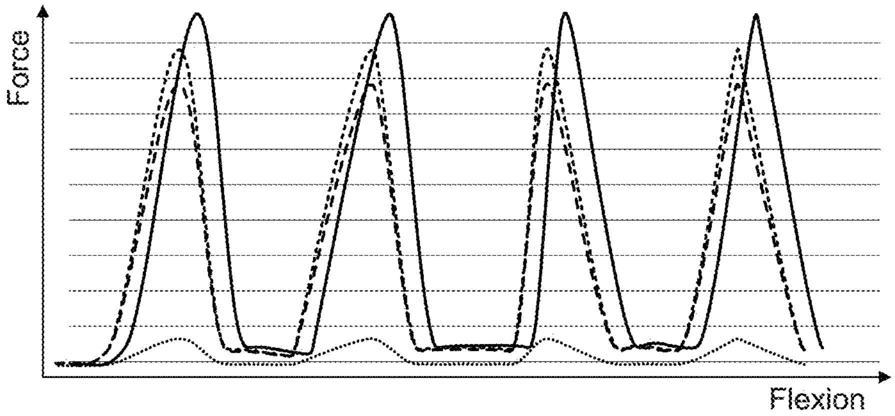

FIGS. 10*a* to 10*c* are graphs which show the variation in load that is sensed by lateral, superior, medial and inferior load sensors on a patella sensor component during flexion, in which the y-axis units reflect the electrical output from the load sensors which is an indication of sensed load.

DETAILED DESCRIPTION

Referring to the drawings, FIG. 1 shows a cutting assembly for resecting a patient's patella during knee surgery. The assembly can be used to locate the depth and inclination of the plane on which the patella is resected in order to prepare it for fitting of a patella implant component. The assembly is also used to support a cutting instrument which is used to perform the resection. As discussed below, the support surface in the assembly shown in FIG. 1 is provided by a slot in a clamp for the patella and is suitable for supporting the blade of a bone saw as commonly used in orthopaedic surgery.

The assembly shown in FIG. 1 has a clamp 2 having a frame 4 in the form of a planar hoop, with first and second ends 6, 8, and first and second sides 10, 12 which extend between the ends. The frame 2 has a first jaw 14 at the first end 10 of the frame and a second jaw 16 at the second end 12 of the frame. The first and second jaws 14, 16 point towards one another on opposite sides of the frame. The second jaw 16 is fixed to the frame at its second end 8. The first jaw 14 is located at the first end 6 of the frame and can slide towards and away from the second jaw 16. A patella can be gripped within the frame by sliding the first jaw 14 towards the second jaw 16 so that teeth on each of the jaws penetrate the tissue of the patella.

The frame has slots 18, 20 formed in it in the two sides 10, 12 which extend between the first and second ends 6, 8. The slots are coplanar so that a saw blade can extend through the first slot 18, across the frame, and through the second slot 20.

The clamp 2 has a stylus arm 22 which extends from the first end of the frame, parallel with the plane of the frame. The stylus arm is mounted on a pivot pin 24 so that it can be rotated about the pin. The stylus arm can be positioned against a patella when the clamp is positioned over a patella with the patella within the frame. The surface of the patella which is contacted by the stylus arm is usually the posterior surface, generally after eversion of the patella. The stylus arm is used as a point of reference for controlling the position of the patella within the frame of the clamp.

The assembly of the invention includes a set of connector inserts 30, 32, 34, a set of spacer inserts 36, 38, 40, and a primary insert 42. Each of the connector inserts has a bore within it whose cross-sectional shape is arranged so that it is a sliding fit on the stylus arm 22. One of the connector inserts 30 is shown in FIG. 1 partially slid on to the stylus arm. Each of the connector inserts has a pair of flexible arms 44 adjacent to the open end of the bore. The arms can be opened so that they can fit around the pivot pin 24 at the end of the stylus arm 22. The connector inserts are formed from a polymeric material which allows the arms to be flexed resiliently so that they tend to restore to their unflexed state so as to engage the pivot pin and retain the connector insert in place on the stylus arm.

Each of the spacer inserts 36, 38, 40 has a hollow body 45 with a continuous top wall 46 and an open bottom face 47. The hollow body 45 can receive the end of one of the connector inserts 30, 32, 34, and has latch features including a pair of flexible latch fingers 48 on its side walls 49 by which any of the spacer inserts can be connected to any of the connector inserts. This is described in more detail below. The bottom face 47 of each of the spacer inserts 36, 38, 40 is provided by a pair of bone engaging flanges 50 which can be positioned against a patella, especially the posterior face of a patella which has been everted.

The connector inserts 30, 32, 34 differ from one another in terms of the inclination of the features by which they engage the stylus arm relative to the features by which they are engaged by a selected one of the spacer inserts. The spacer inserts 36, 38, 40 differ from one another in terms of the distance between the bone engaging flanges and the features by which the spacer inserts engage a selected one of the connector inserts. A spacer insert is selected to provide an appropriate spacing between the plane defined by the slots 18, 20 in the frame 2 and the surface 47 of the spacer insert that is provided by the bone engaging flanges 50. This determines the depth of the portion of bone that is removed from a patella that is located within the clamp 2 between jaws 14, 16, in contact with the bone engaging flanges 50. The selection of an appropriate connector insert determines the inclination of the surface provided by the bone engaging flanges 50 relative to the plane that is defined by the slots 18, 20. This therefore determines the inclination of the plane on which the patella is resected.

The primary insert 42 has an elongate body with a bore within it whose cross-sectional shape is arranged so that it is a sliding fit on the stylus arm 22, similar to the connector inserts 30, 32, 34 as discussed above. The primary insert has a pair of flexible arms 54 adjacent to the open end of the bore which can fit around the pivot pin 24 at the end of the stylus arm to retain the primary insert in place on the stylus arm, in the same way as the arms 44 on the connector inserts 30, 32, 34.

The primary insert has a pair of bone engaging flanges 56 at the end which is opposite the end with the flexible arms 54, for positioning against a patella, especially the posterior face of a patella which has been everted.

Figure 2:
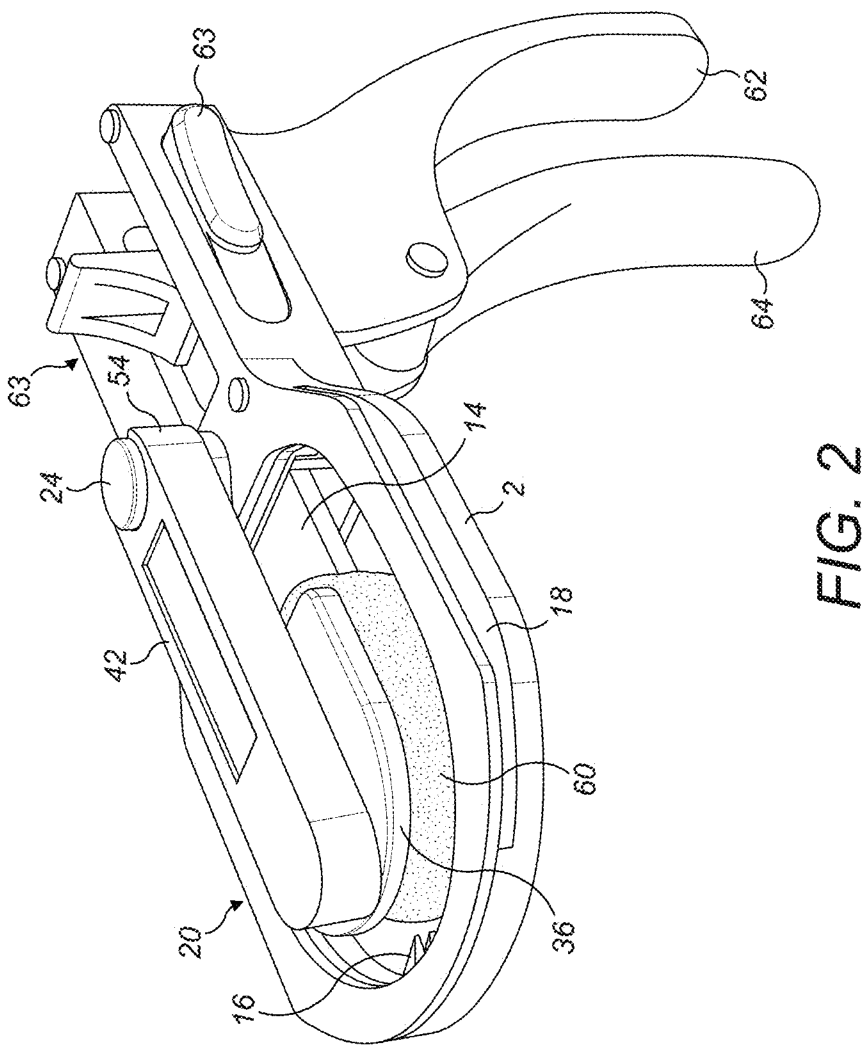
FIG. 2 is an isometric view of the clamp together with a primary insert, positioned in contact with the posterior bearing surface of the patella, prior to resection by means of a bone saw.

FIG. 2 shows the clamp 2 with the primary insert 42 in place, slid fully on to the stylus arm 22 so that the flexible arms 54 are fitted around the pivot pin 24 and the primary insert is retained in place on the stylus arm.

A patella 60, which has been everted, is positioned within the frame 4 of the clamp 2, with its posterior surface against the bone engaging flanges 56 on the primary insert 42. The patella is held in place within the frame of the clamp by means of the jaws 14, 16.

The clamp which is shown in the drawings is sold under the trade mark Premium Patella Saw Guide by Enztech Limited of Christchurch, New Zealand. It has a fixed handle 62 and a pivoting handle 64. The pivoting handle is connected through a hidden ratchet linkage to the first jaw 14. The first jaw 14 can be moved towards the second jaw 16 against the action of hidden return springs by repeatedly squeezing the pivoting handle towards the fixed handle. The clamp has a pair of release buttons 63 which, when pressed together, release the first jaw so that it can retract under the action of the return springs, allowing the patella to be removed from the clamp. The distance between the plane defined by the slots 18, 20 in the frame 4 and the bone facing surface of the stylus arm 22 is 10 mm.

The plane defined by the slots 18, 20 is parallel to the plane that is defined by the bone engaging flanges 56 on the primary insert 42. The distance between the two planes is 4 mm. Consequently the depth of the portion of the patella that is removed posteriorly is about 6 mm. This is less than the depth of conventional patella implant components which frequently have a thickness of 8 mm, or 9 mm, or 9.5 mm, or 10 mm or more. Conventionally, the depth of the portion of the patella that is removed in a resection step corresponds to the thickness of the patella implant component that is to be fitted to the resected patella. The present invention involves an approach in which the patella which has been resected on the initial resection plane following use of the primary insert is assessed to identify the optimum location and inclination for the final resection plane on which the patella implant component is to be fitted. The location and inclination of the final resection plane can be optimised by varying the distance between initial and final resection planes, and the angle between them.

Figure 3:
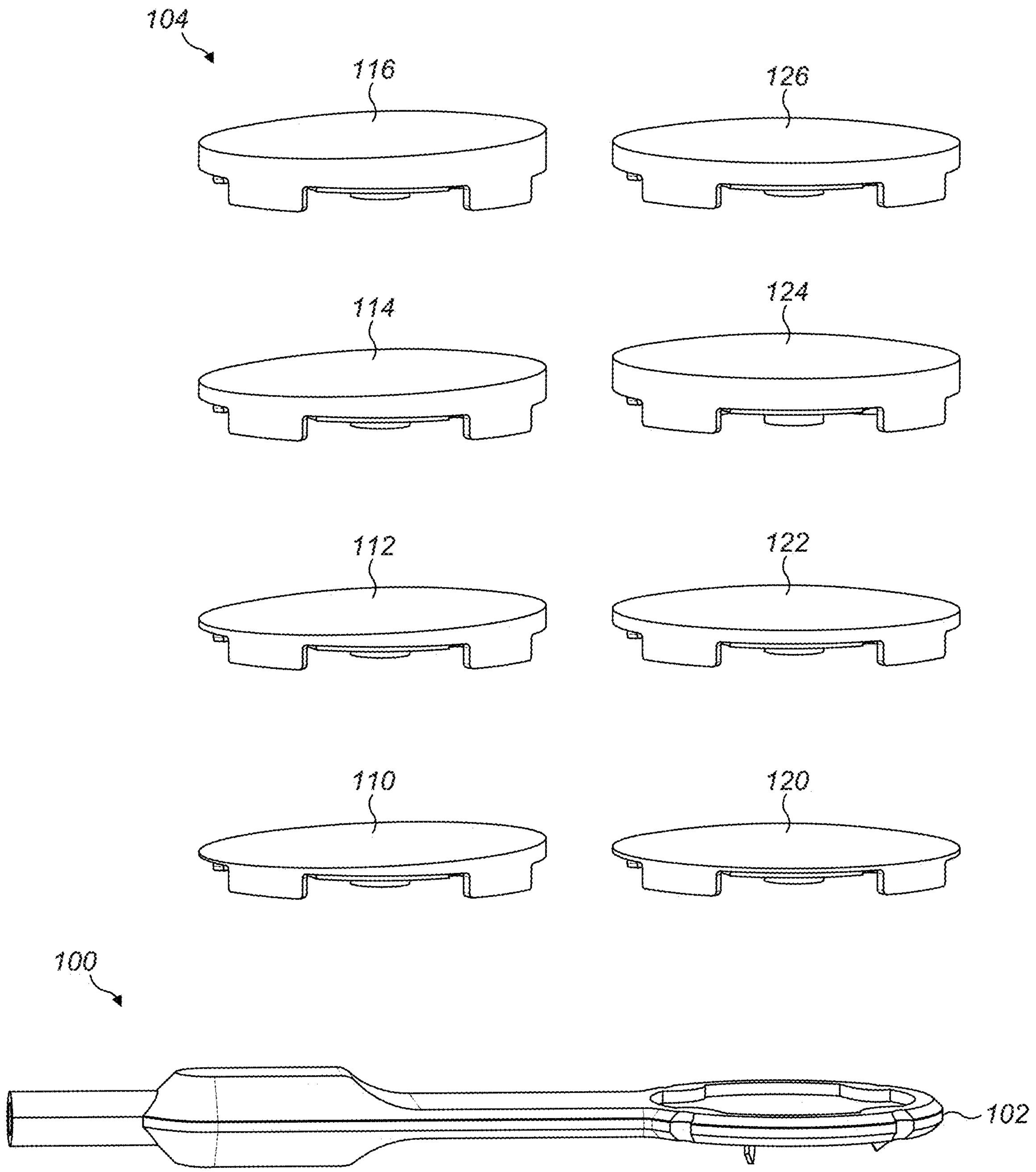
FIG. 3 shows a sensor, a set of shims which can be fitted individually to the sensor.

The resected patella following the initial resection step is assessed using a patella sensor component. FIG. 3 shows a patella sensor component 100 which comprises a backing plate 102 with at least one sensor which can generate a signal corresponding to the compressive load applied to the backing plate. The sensor component includes a set of circular shims 104. Any of the shims can be fitted to the sensor backing plate and can provide a convex dome-shaped patella bearing surface for articulation against the anterior bearing surface on the patient's femur. The shims define different locations or inclinations or both of the patella bearing surface relative to the patella.

The shims are shown in FIG. 3 in two sets of four. In the shims 110, 112, 114, 116 of the first set, the thickness of each shim is constant around the peripheral edge of its bearing surface. The thickness of the shim at the peripheral edge varies between individual shims of the first set, so that the thinnest shim 110 tapers towards zero at its peripheral edge. The thicknesses of the other three shims 112, 114, 116 at their peripheral edges are 1 mm, 2 mm and 3 mm respectively.

In the shims 120, 122, 124, 126 of the second set, the thickness of the shim varies around the peripheral edge of its bearing surface. The angle between the plane defined by the top of the peripheral edge and the plane defined by the bottom of the peripheral edge is greater than zero. In each of the shims 120, 122, 124, 126 of the second set shown in FIG. 3, the angle is 2.5°. Another set of shims might be provided in which the angle between the plane defined by the top of the peripheral edge and the plane defined by the bottom of the peripheral edge has a different value, for example 1.25°.

In each of the shims 120, 122, 124, 126 of the second set, the thickness of the shim is greatest (as a consequence of its convex dome shape) at the centre of the shim. The thinnest shim 120 of the second set tapers towards zero at the point on its periphery where the thickness is at a minimum. The thicknesses of the other three shims 122, 124, 126 of the second set at the point on their peripheries where the thickness is at a minimum are 1 mm, 2 mm and 3 mm respectively.

Figure 4:
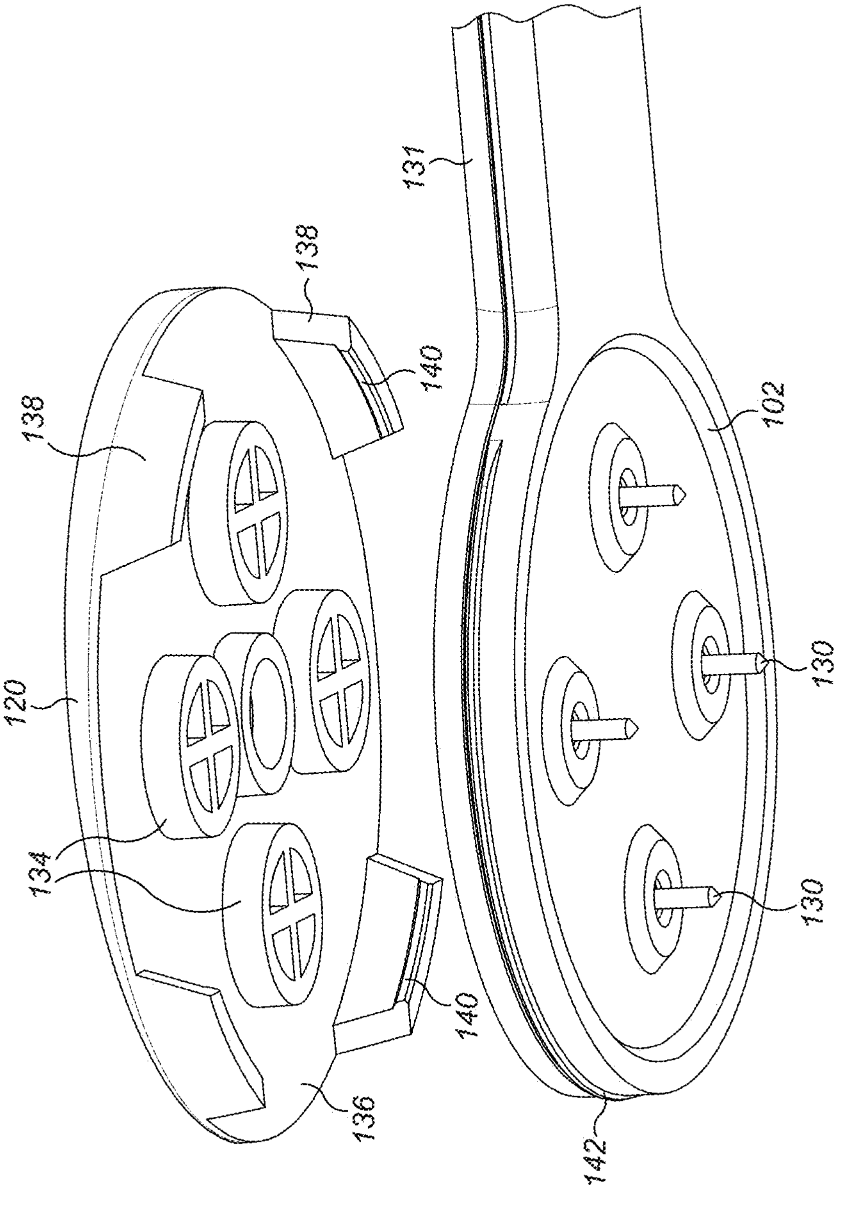
FIG. 4 is an isometric view from below of the sensor shown in FIG. 3 together with a selected one of the shims.

FIG. 4 shows the backing plate 102 of a patella sensor component 100 together with the thinnest shim 120 of the second set of shims. The backing plate caries four sensors 130. The sensor component includes a handle 131 which carries signal wires from the sensors to a data processor.

Any suitable sensors can be used on the backing plate of the patella sensor component. For example, the sensor on the backing plate can comprise a flexible panel which is acted on by a protrusion on the bearing plate so that, when the patella sensor component is placed under a compressive load, the protrusion causes the panel to flex. Preferably, the panel should flex resiliently so that it returns to its unflexed position when a compressive load is removed. The panel can be connected with a strain gauge which can be used to measure the compressive load. It will often be preferred for the backing plate to have at least two flexible panels, especially at least three flexible panels, which are is acted on by respective protrusions on the bearing plate so that, when the patella sensor component is placed under a compressive load, the protrusions cause one or more of the panels to flex, so that the backing plate has at least two sensors or at least three sensors. When there is more than one flexible panel, each such panel can have a strain gauge associated with it to measure the compressive load applied to the patella sensor component. The patella sensor component might incorporate a Wheatstone bridge strain gauge array.

Additionally or alternatively, the backing plate might make use of force sensing resistors to measure a compressive load applied to the patella sensor component. For example, one or more force sensing resistors might be mounted on the backing plate to measure a compressive load applied to the patella sensor component (either integrally or as a separate sensor sheet). Suitable sensors can include piezoresistive force sensors. It is preferred that the sensors are thin and flexible so that they can be incorporated into the trial patella component. Sensors should be selected so that the range of forces that they can sense includes forces which might be sensed in the trial patella component. Preferably the output from the sensor varies linearly with the applied force, at least over the range of forces which might be sensed when the sensor is in use. An example of a force sensor which might be suitable for many applications is the Flexi-Force HT201 sensor, available from Tekscan Inc.

Each of the sensors includes a pin 132 which is pressed against the surface of a patella when the sensor component is in use and ensures that each of the sensors is in physical contact with the patella, notwithstanding any surface irregularities in that surface.

Each of the shims 110, 112, 114, 116, 120, 122, 124, 126 has four protrusions 134 on the surface 136 which faces the backing plate. The protrusions are arranged so that they fit exactly over the sensors 130 on the backing plate. The shims have four deformable fingers 138 which depend from the surface 136 which faces the backing plate. Each of the fingers has an inwardly facing latch 140 at its end.

A selected shim such as the shim 120 shown in FIG. 4 can be positioned over the backing plate 102 so that the protrusions 134 are positioned over the sensors 130 on the backing plate. Pressure applied to the shim to force it on to the backing plate causes the fingers 138 to deform outwardly over the edge of the backing plate. Continued applied pressure causes the shim to move towards the backing plate until the latches 140 on the fingers 138 spring inwardly into a peripheral groove 142 on the backing plate. Reception of the latches 140 in the groove 142 retains the shim on the backing plate. The shim can be released from the backing plate by application of a lifting force to the shim relative to the backing plate.

The orientation of the shim on the backing plate can be varied by rotating the shim successively through angles of 90°. This is advantageous when the shim is from the second set and therefore has a thickness which varies around the peripheral edge of its bearing surface. Rotation of the shim changes the direction of the inclination of the bearing surface, for example from M-L to A-P to L-M to P-A. Intermediate directions are possible by rotating the sensor (backing plate and shim assembly) through an angle of ±45°.

FIG. 5*a* shows a primary insert 200 which has an elongate body 202 with a bore 203 within it whose cross-sectional shape is arranged so that it is a sliding fit on the stylus arm 22. The primary insert has a pair of flexible arms 204 adjacent to the open end of the bore which can fit around the pivot pin 24 at the end of the stylus arm to retain the primary insert in place on the stylus arm.

The primary insert 200 shown in FIG. 5*a* has a constant cross-section along its length. The primary insert has markings 206 on its upper surface which identify the insert, to distinguish it from other inserts. The lower surface 208 of the primary insert 200 provides the reference surface, for positioning against a patella, especially the posterior face of a patella which has been everted. Unlike the primary insert shown in FIG. 1, the primary insert shown in FIG. 5*a* does not have bone engaging flanges on the reference surface at the end which is opposite the end with the flexible arms 204.

The distance between the plane defined by the slots 18, 20 of the frame 4 and the plane defined by the reference surface 208 on the primary insert 200 is 4 mm. This means that, if the arrangement of the stylus arm 22 and the slots 18, 20 is such that, in the absence of an insert on the stylus arm (so that the stylus can contact a patella positioned within the frame), the thickness of the patella tissue that is removed from the patella is 10 mm, the thickness of the patella tissue that is removed when using the primary insert 200 is 6 mm.

FIG. 5*b* shows a neutral connector insert 220. FIG. 5*c* shows an A-P connector insert 222. FIG. 5*d* shows an M-L connector insert 224. Each of the connector inserts 220, 222, 224 has an elongate body 226 with a bore 227 within it whose cross-sectional shape is arranged so that it is a sliding fit on the stylus arm 22 and flexible arms 228 adjacent to the open end of the bore which can fit around the pivot pin 24 at the end of the stylus arm to retain the insert in place on the stylus arm.

The neutral connector insert 220 shown in FIG. 5*b* is open and has flexible arms 228 at one end 230, and continuous upper and lower surfaces 232, 234 extending along the length of the insert. The upper and lower surfaces are essentially planar, and the planes defined by the upper and lower surfaces are perpendicular to the axis defined by the flexible arms, and the pivot pin when the connector insert is in place on the stylus arm. The bore 227 in the connector insert is closed at its other end 236 of the insert. L-shaped grooves 238 are provided in the side walls 240 of the insert towards the closed end 236. The grooves are open on the upper surface 232 of insert. The limb of the L-shaped groove which is open on the upper surface of insert is wider and shorter than the other limb of the groove. The insert has a spring finger 242 in its upper surface adjacent to the L-shaped grooves 238 and a recess 243 in each side wall adjacent to the closed end of each of the L-shaped grooves.

FIG. 5*c* shows an A-P connector insert 222 which is open and has flexible arms 228 at each of its ends 244, 246. It has continuous upper and lower surfaces 248, 250 extending along the length of the insert. The upper and lower surfaces are essentially planar, and the angle between the planes defined by the upper and lower surfaces and a plane which is perpendicular to the axis defined by the flexible arms, and the pivot pin 24 when the connector insert is in place on the stylus arm, is 2.5°. This effectively results in the upper surface 248 of the A-P connector insert being inclined relative to the upper and lower surfaces of the stylus arm 22 when the arm is viewed along its length. The direction of the inclination (right-to-left or left-to-right when the stylus arm is viewed along its length) can be changed by turning the connector insert round through 180°.

The A-P connector insert 222 has two pairs of L-shaped grooves 252 in its side walls 254. The grooves are open on the upper surface 248 of the insert. The insert has spring fingers 250 in its upper surface adjacent to the L-shaped grooves 252 and a recess 255 in each side wall adjacent to the closed end of each of the L-shaped grooves.

FIG. 5*d* shows an M-L connector insert 224 which is open and has flexible arms 228 at each of its ends 256, 258. A transverse step 260 is formed in each of the upper and lower surfaces 262, 263 of the M-L connector insert. The upper and lower surfaces are essentially planar on each side of the step, and the angle between the planes defined by the upper and lower surfaces and a plane which is perpendicular to the axis defined by the flexible arms, and the pivot pin 24 when the connector insert is in place on the stylus arm, is 2.5°. This effectively results in the upper surface 262 of the M-L connector insert being inclined relative to the upper and lower surfaces of the stylus arm 22 when the arm is viewed from one side. The direction of the inclination (right-to-left or left-to-right when the stylus arm is viewed from one side) can be changed by turning the connector insert round through 180°.

Similar to the A-P connector insert 222, the M-L connector insert has two pairs of L-shaped grooves 252 in its side walls 254. The grooves are open on the upper surface 262 of insert. The insert has spring fingers 250 in its upper surface adjacent to each of the L-shaped grooves 252 and a recess 255 in each side wall adjacent to the closed end of each of the L-shaped grooves.

Each of the connector inserts 220, 222, 224 has markings 257 on its upper surface which identify the insert, to distinguish it from other inserts. The markings provide the user with information concerning the inclination of the upper surface of each insert relative to a plane which is perpendicular to the axis defined by the pivot pin 24 when the insert is in place on the stylus arm.

While the A-P and M-L connector inserts which are shown in FIGS. 5*c* and 5*d* are double ended (with flexible arms for engaging the clamp pivot pin, and grooves and a flexible finger for engaging a spacer insert, at both ends), it might be preferred for some situations to provide single ended connector inserts whose appearance will be similar to that of the neutral connector insert shown in FIG. 5*b*. A set of connector inserts will then include two A-P connector inserts in which the inclination angles are +2.5° and −2.5° (or some other value such as 1.25°) respectively, and two M-L connector inserts in which the inclination angles are +2.5° and −2.5° (or some other value such as 1.25°) respectively.

FIGS. 5*e* to 5*g* and FIGS. 6*a* to 6*c* show the spacer inserts 36, 38, 40 which are shown in FIG. 1. Each of them has a hollow body 45 which can be fitted on to a free end of a selected one of the connector inserts 220, 222, 224. FIGS. 6*a* to 6*c* are sectioned isometric views, viewed from below, showing details of the spacer inserts within their hollow bodies.

Each of the spacer inserts 36, 38, 40 has a pair of bone engaging flanges 50 for positioning against a patella, especially the posterior face of a patella which has been everted, and an end wall 265 and a pair of side walls 266. Just one of the side walls can be seen in each of FIGS. 6*a* to 6*c*. The latch fingers 48 provided on each side wall have an inwardly facing detent 264 at its end. Each of the latch fingers 48 includes a lever arm 267 which can be pressed towards the body of the insert.

Each of the spacer inserts 36, 38, 40 has a step 268 in its closed end wall 265 which defines a pocket 270 between the step and the underside of the top wall 269 of the insert.

A locator flange 271 is provided on the inside of the side wall 266 of each spacer insert, adjacent to the latch finger 48. The length of the flange (measured along the axis which extends between the open and closed ends of the insert) is slightly less than the width of the short-open ended limb of the L-shaped groove in each of the connector inserts. The thickness of the flange (measured along the axis which extends between the continuous top wall 46 and the open bottom face 47 of the spacer insert) is slightly less than the width of the long-closed ended limb of the L-shaped groove in each of the connector insert. This arrangement means that a spacer insert can be positioned on the top surface of a connector insert with the locator flanges aligned with the open ends of the L-shaped grooves in the side walls of the connector inserts. The spacer insert can drop on to the connector insert until the locator flange reaches the end of the short limb of the L-shaped groove. The spacer insert can then be slid along the connector insert so that the locator flange slides towards the closed end of the long limb of the L-shaped groove, until the end of the stylus arm 22 is received in the pocket 270 between the step 268 and the underside of the top wall of the insert, and the detent 264 on the latch finger is received in the recess in the side wall of the connector insert. The engagement of the locator flange in the long limb of the L-shaped groove, and the engagement of the end of the stylus arm 22 in the pocket 270, accurately fix the spacer arm against up and down movement relative to the stylus arm.

The spring finger 242 in the top surface of each of the connector inserts presses against the underside of the top wall 269 of the selected spacer insert.

The spacer inserts 36, 38, 40 shown in FIGS. 5*e* to 5*g* and 6*a* to 6*c* differ from one another in terms of the distance between the top wall 269 of the hollow body 45 and the bone engaging flanges 50. The distance is greatest in the spacer insert shown in FIGS. 5*e* and 6*a* and least in the spacer insert shown in FIGS. 5*g* and 6*c*. Each of the spacer inserts has markings 272 on its top wall which is indicative of the distance between the support surface provided by the slots 18, 20 in the clamp and the bone engaging surface provided by the bone engaging flanges 50.

with the spacer insert 36 mounted on a connector insert and the spacer arm 22, the distance between the plane defined by the slots 18, 20 of the frame 4 and the plane defined by the bone engaging surface provided by the bone engaging flange 50 is 9 mm. This means that, if the arrangement of the stylus arm 22 and the slots 18, 20 is such that, in the absence of an insert on the stylus arm (so that the stylus can contact a patella positioned within the frame), the thickness of the patella tissue that is removed from the patella is 10 mm, the thickness of the patella tissue that is removed when using the spacer insert 36 is 1 mm, making a total resection of 7 mm when the resection using the primary insert is 6 mm.

with the spacer insert 40 mounted on a connector insert and the spacer arm 22, the distance between the plane defined by the slots 18, 20 of the frame 4 and the plane defined by the bone engaging surface provided by the bone engaging flange 50 is 7 mm. This means that, if the arrangement of the stylus arm 22 and the slots 18, 20 is such that, in the absence of an insert on the stylus arm (so that the stylus can contact a patella positioned within the frame), the thickness of the patella tissue that is removed from the patella is 10 mm, the thickness of the patella tissue that is removed when using the spacer insert 40 is 3 mm, making a total resection of 9 mm when the resection using the primary insert is 6 mm.

The amount of bone removed using different combinations of the spacers shown in the drawings is as follows:

| Shim | Insert which contacts patella | Depth of resection | Total depth of removed bone | Relative location of patella implant posterior surface |
|---|---|---|---|---|
| 0 mm (110) | Primary insert (42) | 6 mm | 6 + 0 = 6 mm | +3 mm |
| 1 mm (112) | Spacer insert (36) | 1 mm | 6 + 1 = 7 mm | +2 mm |
| 2 mm (114) | Spacer insert (38) | 2 mm | 6 + 2 = 8 mm | +1 mm |
| 3 mm (116) | Spacer insert (40) | 3 mm | 6 + 3 = 9 mm | 0 |

The first column in the table identifies shims that might be used with the backing plate to identify the optimum soft tissue tension across the knee joint. This informs the surgeon as to which of the spacer inserts should be used in a second resection step (if that is required). In the example set out in the table, the shim is one whose thickness is constant around its peripheral edge (110, 112, 114, 116). The connector insert to which a selected one of the spacer inserts is mounted is the neutral connector insert 220.

In another example, the shim might be one whose thickness varies around its edge (12, 122, 124, 126), with an inclination angle between the plane defined by the top of the peripheral edge and the plane defined by the bottom of the peripheral edge is greater than zero, for example 1.25° or 2.5°. In this case, the connector insert will be one which be an A-P connector insert or an M-L connector insert, for example as shown in FIGS. 5*c* and 5*d*.

The second column in the table identifies the insert which is provided on the stylus arm and which provides the surface for contacting the patella to locate the patella in the clamp during the resection step. It is the primary insert 42 in the initial cut which removes 6 mm of bone from the posterior of the patella, including the native patella bearing surface. It is one of the spacer inserts 36, 38, 40 in a second cut (if required) which removes an additional 1 mm, 2 mm or 3 mm layer of bone, as noted in the third column.

The last column in the table indicates the location of the posterior surface of a patella implant which is fitted to the resected patella, relative to the posterior surface of the patella prior to the procedure. In this example, the thickness of the patella implant that is used is 9 mm. By way of explanation, when the spacer insert 38 is used in the second resection step, the position of the posterior surface of the patella implant is 1 mm posterior of the native patella posterior surface. This can be appropriate to increase tension in soft tissue attached to the patella (such as the quadriceps muscle), for example because the anterior facing portion of the femoral bearing surface is located posteriorly of the native femoral bearing surface.

The orientation of the inclination of the plane of the second resection can be selected by selection of an appropriate connector insert, so that the second resection plan is inclined on the A-P axis or on the M-L axis. The orientation can be fine tuned by rotating the clamp relative to the patella (before the patella is gripped between the jaws 14, 16) through an angle of ±45°.

A spacer insert which is fitted to the A-P connector insert 222 or the M-L connector insert 224 masks one of the sets of markings on the connector insert. This means that, once the spacer insert has been fitted to the connector insert, a surgeon is able to read from the assembled inserts the information concerning the inclination of the resection plane in the patella from the markings on the connector insert that continue to be visible, and the depth of the resection from the markings on the spacer insert.

A spacer insert can be released from a connector insert to which it is connected by squeezing the latch fingers 48 towards one another and towards their respective side walls. By a lever action, this causes the detents 264 on the latch fingers to release from the recesses in the side walls of the connector insert so that the spacer insert can be slid along the connector insert. The locator flange thereby slides along the long limb of the L-shaped slot. The spacer insert can then be lifted off the connector insert, with the locator flange sliding along the short limb of the L-shaped slot.

A connector insert can be released from engagement with the pivot pin 24 by pulling the insert along the stylus arm 22, causing the flexible arms on the connector insert to splay.

FIG. 7 shows the neutral angle connector insert 220 and the spacer insert 38, with the spacer insert fully engaged with the connector insert, as described above.

FIG. 8 shows the neutral angle connector insert 220 and the spacer insert 38 assembled on the stylus arm 22 of the clamp 2, with an everted patella 300 held within the clamp by means of the jaws 14, 16, and the bone engaging flange 50 on the spacer insert 38 engaging the posterior surface of the patella.

FIG. 9*a* shows a patient's knee joint schematically, showing the femur 500 and the tibia 502 with the native femoral and tibial bearing surfaces intact. The patella 504 has been resected to a depth of 6 mm using the primary insert 42 on the clamp, as described above.

The patella sensor component 100 is positioned against the posterior resected surface of the patella. The sensor component has a shim 110 clipped to it. The shim is the thinnest of the shims of the first set, having a constant thickness around its peripheral edge. The thickness of the patella sensor component as used at this stage in the procedure is 6 mm, and is therefore the same as the thickness of the patella tissue that is removed in the initial resection step. The joint can be flexed with the sensor component in place on the posterior face of the patella and information about the compressive forces to which the sensor component is subjected can be obtained from the sensors 130 on the backing plate of the sensor component which can be seen in FIG. 4.

FIG. 10*a* is a graph which shows how the compressive force that is measured using each of the sensors 130 varies during articulation of the joint.

FIG. 9*b* shows the patient's knee joint after preparation of the femur and the tibia and fitting of a femoral trial component 510 and a tibial trial component 512. The surgical steps to prepare the femur and the tibia are well known. FIG. 9*b* shows the patella sensor component 100 positioned against the posterior resected surface of the patella, with the same shim 110 clipped to the sensor component as in the assessment of the native joint as shown in FIG. 9*a*. Flexing the joint provides information about changes in the compressive forces to which the patella sensor component is subjected as a result of the surgical steps to fit the femoral and tibial trial components. Changes to the forces to which the patella sensor component is subjected give rise to corresponding changes in the soft tissue by which the patella is held in place, notably the quadriceps muscle. The present invention enables such changes to be identified and to be minimised.

FIG. 10*b* is a graph showing how the compressive force that is measured using the sensors 130 varies during articulation of the joint when the femoral and tibial trial components 510, 512 are in place. In this example, it can be seen that the compressive forces are reduced compared with those measured in the native joint. This might be for example because the anterior bearing surface provided by the femoral trial component is located posteriorly relative to the bearing surface provided by the native femur. A consequence is that the tension in soft tissue attached to the patella is reduced. This can compromise the surgical outcome, for example with the possibility of patellofemoral pain.

FIG. 9*c* shows the patient's knee joint with the femoral and tibial trial components 510, 512 in place, and with a shim 116 attached to the backing plate 102 of the patella sensor component in the place of the shim 110 shown in FIGS. 9*a* and 9*b*. As discussed above, the shim 116 which is shown in FIG. 9*c* is thicker than the shim 110 which is shown in FIGS. 9*a* and 9*b*. This results in the patella being located more anteriorly relative to the femur compared with its position in the arrangements shown in FIG. 9*b*, so that the compressive forces to which the patella sensor component is subjected, and the tension in the soft tissue attached to the patella, are increased. The compressive forces to which the sensor component is subjected are depicted in the graph in FIG. 10*c*.

Use of the components provided by the invention can involve identifying the shim (which might be any of the shims shown in FIG. 3) which, when attached the backing plate as shown in FIG. 9*c*, gives rise to variations in the compressive forces which most closely match the variations in the native knee as shown in FIG. 10*a*. This enables the surgeon to select connector and spacer inserts for use with the clamp to perform a second resection. The inserts are selected by an analysis such as that described above with reference to the data in the table.

Patella implant components are frequently rotationally symmetrical. This can mean that the surgeon does not have to consider the rotational orientation of a patella implant component when positioned on a resected patella. Some patella implant components might not be rotationally symmetrical. For example, the apex of a domed patella implant component might be located closer to one edge than to an opposite edge. The assembly of the invention can be used to identify an optimum rotational orientation for such an implant component, in which the forces to which it is subjected, and which are applied to the surface of a femoral implant component with which the patella implant component articulates, are appropriately balanced.

The invention claimed is:

1. An assembly for use in knee surgery, which comprises:
- a. a patella sensor component comprising:
  - i. a backing plate which can be fitted to a patella and which has at least one sensor which can generate a signal corresponding to a compressive load applied to the backing plate,
  - ii. at least first and second shims which provide a patella bearing surface for articulation against a surface on a patient's femur, and which can be positioned individually or in one or more combinations on the backing plate so as to face the patient's femur, the combinations defining first and second positions of the bearing surface relative to the patella,
- b. a cutting instrument having a cutting head for cutting the patella on a selected resection plane,
- c. a clamp for a patella having opposing jaws which can be moved towards one another to clamp the patella between them, the clamp providing:
  - i. a reference surface for engaging a posterior surface of the patella,
  - ii. a support surface for supporting the cutting head of the cutting instrument, thereby locating the cutting instrument relative to the clamp,
- d. at least first and second locator inserts which can be mounted individually or in one or more combinations on or relative to the clamp, providing a physical connection between the reference and support surfaces which define first and second positions of the support surface relative to the reference surface, and thereby define first and second positions for the resection plane relative to the posterior surface of the patella, in which an increment between the first and second positions of the bearing surface defined by the combinations of the first and second shims relative to the patella matches the increment between the first and second positions of the support surface relative to the reference surface.

2. An assembly as claimed in claim 1, which includes a third shim which can be used to define a third position of the bearing surface relative to the patella, and a third locator insert which can be used to define a third position of the bearing surface relative to the patella, and in which an increment between the second and third positions of the bearing surface relative to the patella matches the increment between the second and third positions of the support surface relative to the reference surface.

3. An assembly as claimed in claim 1, in which a thickness of the second shim is greater than a thickness of the first shim, and a difference in thickness between the first and second shims matches a difference between the distances between the reference surface and the support surface when in their first and second relative positions.

4. An assembly as claimed in claim 1, in which each shim has principal opposite surfaces and an angle between the principal surfaces of the second shim is greater than the angle between the principal surfaces of the first shim, and the difference between the angles between the principal surfaces of the first and second shims matches the difference between the angles between the reference surface and the support surface when in their first and second relative positions.

5. An assembly as claimed in claim 1, in which each of the first and second locator inserts comprises a connector insert which can be mounted on the clamp and a spacer insert which can be mounted on the connector insert.

6. An assembly as claimed in claim 5, in which each shim has principal opposite surfaces and an angle between the principal surfaces of the second shim is greater than the angle between the principal surfaces of the first shim, and in which the difference between the angles between the reference surface and the support surface when the first and second connector inserts respectively are mounted on the clamp matches the difference between the angles between the principal surfaces of the first and second shims.

7. An assembly as claimed in claim 5, in which a thickness of the second shim is greater than a thickness of the first shim, and in which the assembly includes first and second spacer inserts, and in which a difference in distances between the reference surface and the support surface when the first and second spacer inserts respectively are in mounted on the clamp matches a difference between the thicknesses of the first and second shims.

8. An assembly as claimed in claim 1, in which the backing plate and the shims include cooperating engagement features by which shims can be fastened to the backing plate.

9. An assembly as claimed in claim 1, which includes a patella implant component.

* * * * *